United States Patent [19]

Behan et al.

[11] Patent Number: 5,156,766

[45] Date of Patent: Oct. 20, 1992

[54] STABILIZED EMULSION SYSTEMS

[75] Inventors: John M. Behan, Kennington; Jeremy N. Ness, Chartham; Keith D. Perring, Ashford; William M. Smith, Folkstone, all of Great Britain

[73] Assignee: Unilever Patent Holdings, B.V., Rotterdam, Netherlands

[21] Appl. No.: 727,634

[22] Filed: Jul. 10, 1991

[30] Foreign Application Priority Data

Jul. 11, 1990 [EP] European Pat. Off. ........ 90307586.9

[51] Int. Cl.$^5$ .............................................. B01J 13/00
[52] U.S. Cl. .................... 252/312; 252/315.4; 252/351; 252/358; 424/450
[58] Field of Search ...................... 252/312, 315.4, 351, 252/358; 424/450

[56] References Cited

U.S. PATENT DOCUMENTS

| 4,097,403 | 6/1978 | Tsutsumi et al. | 252/312 |
| 4,217,344 | 8/1980 | Vanlerberghe et al. | 424/60 |
| 4,508,703 | 4/1985 | Redziniak et al. | 424/38 |
| 4,536,324 | 8/1985 | Fujiwara et al. | 252/311 |
| 4,670,185 | 6/1987 | Fujiwara et al. | 252/311 |
| 4,772,471 | 9/1988 | Vanlerberghe et al. | 424/450 |
| 4,830,857 | 5/1989 | Handjani et al. | 424/450 |
| 4,897,308 | 1/1990 | Vanlerberghe | 428/402.2 |
| 4,942,038 | 7/1990 | Walbach | 424/450 |
| 5,021,200 | 6/1991 | Vanlerberghe et al. | 264/43 |
| 5,041,283 | 8/1991 | Kita et al. | 424/64 |

FOREIGN PATENT DOCUMENTS

| 0217105 | 4/1987 | European Pat. Off. . |
| 0316726 | 5/1989 | European Pat. Off. . |
| WO9001921 | 3/1990 | European Pat. Off. . |
| 0368146 | 5/1990 | European Pat. Off. . |
| 1439244 | 6/1976 | United Kingdom . |

OTHER PUBLICATIONS

Chemical Abstracts, vol. 104, 1986, p. 302, 104:10406s.
Lochhead et al, Novel Cosmetic Emulsions; Cosmetics & Toiletries, Nov. 1986, vol. 101, pp. 125-137.
DATABASE WPI(L), AN=87-014988 [03], Derwent Publications Ltd., London, GB, AB=DD-239116 (Abstract).
DATABASE WPI(L), AN=78-59474A [33], Derwent Publications Ltd., London, GB, AB-J53079043 (Abstract).
DATABASE WPI(L), AN=89-066015 [09], Derwent Publications, Ltd., London, GB, AB-J01019004 (Abstract).

Primary Examiner—Richard D. Lovering
Assistant Examiner—N. Bhat

[57] ABSTRACT

The invention concerns emulsions based on non-ionic emulsifiers, with improved stability achieved by the addition of selected perfumery materials, and a process for preparing such emulsions. The emulsions comprise 1-30% by weight of one or more non-ionic emulsifiers 30-98% of an aqueous phase and 0.01-50% of hydrophobic materials. The stabilizing perfumery materials are present in 0.5-25% by weight based on the non-ionic emulsifiers. The emulsions are preferably prepared under low shear.

16 Claims, No Drawings

STABILIZED EMULSION SYSTEMS

FIELD OF THE INVENTION

The present invention relates to emulsion systems containing nonionic emulsifiers. It relates more specifically to such emulsions which are stabilized by the inclusion therein of selected perfumery materials, and to a process for preparing such emulsions.

DESCRIPTION OF RELATED ART

Emulsions find very common application in the cosmetics, toiletries and household products fields. There is thus a large amount of related art describing these systems, particularly in relation to the correct choice of emulsifying materials, co-emulsifiers, stabilisers and in the methods of production of such systems to maximise both stability and performance. The stability of emulsion systems can be controlled by a variety of parameters, e.g. as taught by Tadros and Vincent in "Encyclopedia of Emulsion Technology", Marcel Dekker, New York (1983), Vol. 1, Chpt 3. It is important to use emulsifying systems that possess the correct hydrophilic-lipophilic balance (HLB) to produce the most stable emulsion for a particular hydrophobic material. One of the most common groups of emulsifiers found in the field of cosmetics, toiletries and household products comprises non-ionics. These are preferred in many cases because of their compatibility with a wide range of other materials (e.g. cosmetic actives) and because of their relatively low toxicity and irritancy.

Further, it is possible to produce greater stability using mixtures of emulsifying materials, co-solvents and additives, e.g. additives with the potential to stiffen any liquid crystal structure that may be present. The presence of liquid crystals in various emulsion systems has been well-established for some time, and the potential for increased emulsion stability has been noted, see, for example, the papers of S.Friberg et al in J. Colloid Interface Sci., 37, page 291, 1971 and 55, page 614, 1976, and also J. Boyd, P. Sherman and N. Krog in "Theory and Practice of Emulsion Technology", (A.L. Smith, ed.) Academic Press, New York (1974), page 37.

Particular advantage has been taken of those nonionics that form liquid crystals to form so-called 'niosomes' (nonionic surfactant liposomes), whereby a second phase (usually aqueous) is encapsulated within a liquid crystal coating. This is illustrated in a variety of cases, e.g. U.S. Pat. No. 4,217,344 (L'Oreal), U.S. Pat. No. 4,536,324 (Lion Corp.), WO 88/06881 (Micro-Pak Inc.). The use of such systems in skin creams is decribed by G. Dahms in "Cosmetics and Toiletries", Vol 101, no. 11 (1986), pp.113–115. Although the internal encapsulated phase is usually aqueous, WO 88/06883 (Micro Vesicular Systems) teaches that it is possible to enclose non-aqueous/hydrophobic materials in so-called paucilamellar lipid vesicles. In this system, the lipid vesicles can be considered to be an example of a classical oil-in-water emulsion where the emulsifier phase is discontinuous.

Application is often made in niosome systems of additives which allow increased stability. As taught in WO 88 06882 (Micro Vesicular Systems), they serve to both stiffen the liquid crystal layers and to help buffer the thermotropic phase transition as temperatures are changed, thus improving the thermal stability. The most common additive used for this purpose is cholesterol, although other sterols are known to give the same effect, and certain derivatives such as cholesterol phosphate (see GB 2,189,457, L'Oreal), and cholesterol sulphate (see GB 2,198,947, L'Oreal) are also useful as stabilisers. Finally, EP 316 728 and EP 368 146 describe clear microemulsion cleaning compositions comprising anionic and nonionic surfactants, co-surfactants, perfume and water. These products are intended for removing oily and greasy soils.

Both classical emulsions and niosomal systems are usually marketed as products which include a perfume. In general, such perfumes are added solely to impart aesthetic appeal to the product, although in some cases additional functional benefits have been claimed, e.g. aromatherapeutic effects, preservative action, insect repellency. Niosomal systems with a high perfume concentration are described in EP 347 306, which appear to contain separate bubbles of non-ionic emulsifier (based on polyglycerol derivatives) and droplets of perfume, surrounded by a continuous aqueous phase.

Nothing in the prior art suggests that perfumes or perfumery materials could be used to improve emulsion stability.

SUMMARY OF THE INVENTION

It is an object of the present invention to provide emulsions based on non-ionic emulsifiers, with improved stability achieved by the addition of selected perfumery materials. It is a further object of the invention to provide stable emulsions with the added benefit of having an agreeable odour. It is still another object of the invention to obviate the need for emulsion stabilizers such as cholesterol, cholesteryl esters, other sterol or sterol derivatives or polymers designed to prevent agglomeration of emulsion droplets, through stabilization of an emulsion with perfumery materials. It is yet another object of the invention to extend the useful lifetime of an emulsified product by making it more robust and less sensitive to fluctuations in its physical state (e.g. temperature) and to give it an agreeable odour at the same time by adding thereto a perfume comprising selected perfumery materials.

The invention provides stable emulsions based on non-ionic emulsifiers as the emulsifying agent, containing as stabilizing agents perfumery materials which pass the test for stabilizing ability which is hereinafter described. The invention also provides a process for preparing such emulsions.

DETAILED DESCRIPTION OF THE INVENTION

The emulsions of the invention comprise a non-aqueous phase (P), comprising the following components:
(a) An emulsifier system A, consisting of one or more non-ionic emulsifiers;
(b) A liquid hydrophobic system B, consisting of one or more hydrophobic materials;
(c) One or more stabilizing perfumery materials C;
(d) One or more optional surfactants D, other than non-ionics;
and an aqueous phase E, optionally also comprising water-soluble or water-dispersible materials.

The emulsions of the invention are opaque and are prepared according to the following process:
I. the non-aqueous phase P, is formed by mixing the emulsifier system A with the hydrophobic system B, the stabilizing perfumery materials C and optional surfactants D, whilst maintaining the temperature at as sufficiently high level to obtain a homogeneous liquid.

II. The non-aqueous phase P and the aqueous phase E, which is maintained at substantially the same temperature as P, are added together and mixed under shear conditions for a sufficient time to obtain a stable emulsion and bringing the mixture to ambient temperature if necessary.

In this connection "homogeneous" is defined as the absence of discrete solid particles or droplets of liquid in the non-aqueous phase. Also, "substantially the same temperature" is intended to mean such temperature that after mixing of aqueous and non-aqueous phase the complete emulsion has a temperature at which the non-aqueous phase would have formed a homogeneous liquid.

The emulsifier system is preferably used in an amount of 1–30% by weight of the total emulsion, more preferably 4–25%, particularly 10–20%. The non-ionic emulsifiers therein are suitably chosen from:

i.a. (Polyethoxylated) fatty alcohols of the formula:

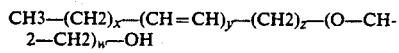
$$CH_3-(CH_2)_x-(CH=CH)_y-(CH_2)_z-(O-CH_2-CH_2)_w-OH$$

wherein: w ranges from 0–20, preferably from 0–6, more preferably from 0–2 or 2–4; y is 0 or 1; $x+z+2y=11-23$, preferably 11–17.

i.b. Branched (polyethoxylated) fatty alcohols of the formula:

$$R-(O-CH_2-CH_2)_x-OH$$

wherein: R is a branched alkyl group of 12–18 carbon atoms and w is as specified above.

ii. Glycerol mono-fatty acid esters, particularly glycerol mono-stearate, oleate, palmitate or laurate.

iii. Fatty acid esters of polyethylene glycol, particularly those of the formula:

$$R1-(O-CH_2-CH_2)_w-OH \text{ or}$$

$$R1-(O-CH_2-CH_2)_w-O-R1$$

wherein R1 is a stearoyl, lauroyl, oleoyl or palmitoyl residue; w ranges from 2–20, preferably from 2–8.

iv. Sorbitan fatty acid esters, particularly the mono-and tri-esters of the formula:

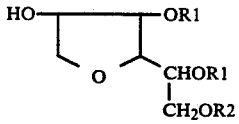

wherein: R1 is H or

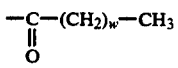

and R2 is

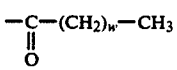

and w ranges from 10–16; preferably w is 16.

v. Polyethoxylated sorbitan fatty acid esters, particularly those of the formula:

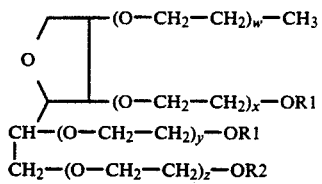

wherein: R1 is H or

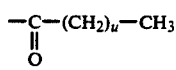

and
R2 is

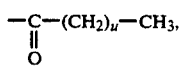

u ranges from 10–16 and average $(w+x+y+z)$ is 2–20. Preferably, u is 16 and average $(w+x+y+z)$ is 2–4.

The aqueous phase consists of water or an aqueous mixture containing water-soluble materials or water-dispersible materials, hereinafter called "hydrophilic materials". Such materials may be present as humectants, preservatives, stabilisers, colouring agents, salts, thickeners, emollients, conditioners, anti-oxidants, water-soluble perfume and therapeutic agents. The hydrophilic materials preferably constitute no more than 30% by weight of the aqueous phase. The total aqueous phase is preferably present at a level of 30–98%, more preferably 40–95% by weight of the total emulsion.

The non-aqueous phase P contains one or more hydrophobic materials (jointly called "hydrophobic system") at a level of 0.01–50% of the total weight of the emulsions, more preferably 10–50%, particularly 10–40%. The term "hydrophobic" is taken to denote a material which will be soluble in one or more organic solvents such as acetone, ethanol or hydrocarbon solvents, and will not exhibit an appreciable degree of solubility in water. Examples of suitable materials include perfumes, essential oils, oil-soluble polymers, emollients, sunscreens, anti-wrinkling agents, dyes, colourants, astringents, humectants, preservatives, anti-oxidants, and conditioners. It is not essential that all the hydrophobic materials in the non-aqueous phase be liquid, provided that their mixture forming the hydrophobic system is liquid. Thus, for example, perfumes and sunscreens which happen to be solid at ambient temperatures may be used provided that they are admixed with other hydrophobic components to form a homogeneous liquid. Perfumes are particularly suitable as the only or main component of the hydrophobic system.

Optional surfactants (other than non-ionics) may be added to the non-aqueous phase in all cases, but are preferably used to aid in the formation of liquid crystalline structures and added at a level of 0–50% of the weight of the non-ionic emulsifier(s). Examples of suitable surfactants include quaternary ammonium compounds (e.g. cetyltrimethyl ammonium bromide and chloride), anionics (e.g. sodium lauryl sulphate and sodium dodecylbenzenesulphonate) and organophosphate esters (e.g. dicetyl phosphate). Preferably the amount of optional surfactant is not more than 20% by weight, more preferably 10% or less, relative to the non-ionic emulsifier(s).

Stabilizing perfumery materials are perfumery materials with a sum score of at least 4+'s and preferably at least 5 +'s in the test for stabilizing ability which is described below. They are incorporated in the non-aqueous phase of the emulsion to be stabilized at a level of 0.5-25% of the weight of the non-ionic emulsifier(s), preferably at a level of 5-15%.

For the purpose of this invention perfumery materials are defined as those materials which are known in the art of perfumery to be useful as ingredients for perfumes and are less than 10% soluble in water. As used herein the term "perfume" denotes a mixture of perfume ingredients, which mixture is used to impart a desired odour to the skin and or to products to which they are added. Most ingredients for perfumes are included therein because of their contribution to the odour of the perfume, some ingredients may be included because of other properties such as their solvent or diluent properties or their fixative effect. Well known perfume ingredients are mentioned e.g. in S. Arctander, "Perfume and Flavor Chemicals, Montclair, N.J., U.S.A. (1969), and in "Flavor and Fragrance materials —1989", Allured Publ. Corp. Wheaton, Il, USA.

The stabilizing perfumery materials may be used as such as a component of the non-aqueous phase. They may also first be added to the liquid hydrophobic system, either as such or as part of a perfume which also comprises non-stabilizing ingredients. Even if the non aqueous phase already contains materials which enhance emulsion stability, e.g. as part of the hydrophobic system, the addition of (more) stabilizing perfumery materials may further improve emulsion stability. However, stabilizing perfumery materials which are not made part of the non-aqueous phase before preparing the emulsion, but instead are added to the emulsion afterwards, either as such or as part of a complete perfume, hardly have any stabilizing effect in the emulsion, presumably because they are not integrated into the liquid crystal structure, but largely remain on the outside of the emulsion droplets and in the continuous phase.

For the mixing of the non-aqueous and the aqueous phase, the order of mixing is not critical, although normally the non-aqueous phase is added to the aqueous phase. In addition, although the shear rate used for mixing will affect to some extent the ultimate droplet size of the emulsion, the actual shear rate used is not critical in most cases for formation of the emulsion. Use of too high a shear rate with relatively viscous emulsions can result in destabilisation of the emulsion system. The emulsions of the invention are suitably prepared under conditions of low shear, using mixers providing shear rates within the range of 10-1400s$^{-1}$ Preferred shear rates lie within the range of 15-500s$^{-1}$ which values are considerably lower than those provided by high shear mixers / homogenisers such as Microfluidisers (trademark of Microfluidics Corp.). Suitable information on shear rates and fluid behaviour in mixing vessels can be found in Perry's Chemical Engineer's Handbook, sixth edition, D. Green (editor), McGraw-Hill, 1984. Thus, although both high and low shear rate mixers can be used, low shear rate mixers are generally preferred (even laboratory magnetic stirrers are suitable), so obviating the need for complicated and expensive equipment and improving the economics of the process. The resulting emulsions are opaque and will generally have a droplet diameters of 0.2 $\mu$m and higher, with the majority of them (on a weight basis) having a droplet diameter above 1 $\mu$m.

Emulsions according to the invention are excellently suitable as cosmetics, toiletries and household products, such as skin creams, hand and body lotions personal perfumes, body deodorants, liquid toilet soaps, bath oil products, hair conditioners, fabric conditioners, general purpose cleaners, etc. In addition to these direct uses of the emulsions according to the invention, the emulsions are also suitable for incorporation into a variety of aqueous products such as tooth pastes, mouth washes, shampoos, hair conditioners, fabric conditioners and shower gels. On addition to such products the emulsion breaks down into vesicular droplets/liposomes, characterized by lipid bilayers structured by perfumery materials as stabilizers and surrounding a core comprising hydrophobic and/or aqueous liquid, according to the constitution of the original stabilized emulsion. The size of the vesicles will depend upon the nature of the product's composition and the method of incorporation. Emulsions according to the invention wherein perfumes are the only or main component of the liquid hydrophobic system are very suitable for delivering perfumes to cosmetics toiletries and household products.

Test for stabilizing ability

Five different test emulsions are made up according to the following procedure :

| Non-aqueous phase: | 5.00 g hydrophobic material |
| --- | --- |
|  | 1.00 g non-ionic emulsifier |
|  | 0.15 g perfumery material |
| Aqueous phase: | 20.0 g water |

The non-aqueous phase is heated to form a homogeneous liquid, whilst heating the water to the same temperature. The water is mixed into the non-aqueous phase with stirring and stirring is continued whilst cooling to room temperature. A control emulsion is prepared according to the same procedure but containing the same level of cholesterol as emulsion stabilizer.

After storage for 24 hours at room temperature, the test and the control emulsion are brought to and held at the test temperature (see below) until physical separation of a continuous oil phase begins to occur in either of the emulsions. Separation of emulsion particles under gravity (e.g. 'creaming') does not constitute separation of a continuous oil phase, but will be heavily dependent upon the densities of the water and non-aqueous phases, and does not necessarily indicate that the emulsion particles have agglomerated or suffered other deleterious changes.

Those test emulsions wherein the perfumery material produces no more separation than the control are rated +for equal performance to cholesterol, or + +for superior performance, those emulsions producing more separation than the control containing cholesterol are rated —. Control emulsions by definition score +. Perfumery materials which score at least 4 +'s in this test are of general utility as emulsion stabilisers in emulsions in the fields of cosmetics, toiletries and household products, those scoring less than 4 +'s may still be useful in certain areas.

The non-aqueous phases and test temperatures for the five test emulsions are:
1. Perfume A (see Table 1); Brij 52; test temperature =45° C.
2. Isopropyl myristate; glycerol monostearate; test temperature =75° C.
3. Petroleum Jelly; Span 20; test temperature =50° C.
4. Mineral oil; Tween 21; test temperature =40° C.
5. Mineral oil/isopropyl myristate (1:1); Citrol 4MO; test temperature =50° C.;

The test temperatures were chosen such that they lie 10° C. to 40° C. above the melting points of the non-ionic emulsifiers and the final choice was made on the basis of convenience (e.g. longevity of the test).

TABLE 1

(Formulation of Perfume A)

| Ingredient | Weight (g) |
|---|---|
| Benzyl benzoate | 24.50 |
| Alpha-pinene | 6.60 |
| Rose oxide | 2.00 |
| 3,6-Dimethyloctan-3-ol | 6.00 |
| Cinnamyl acetate | 5.60 |
| Litsea Cubeba | 0.95 |
| n-Amyl acetate | 0.70 |
| Lemon oil Spanish | 4.80 |
| Alpha-hexylcinnamic aldehyde | 2.00 |
| Alpha-terpineol | 4.85 |
| Ethyl acetoacetate ethylene glycol ketal | 7.20 |
| Orange oil sweet Florida | 1.10 |
| 1,1,2,4,4,7-Hexamethyl-6-acetyltetralin | 1.50 |
| 2-Phenylethanol | 10.00 |
| Limonene | 6.20 |
| Linalyl acetate | 8.00 |
| Vanillin | 3.00 |
| Thymol | 1.00 |
| Benzyl alcohol | 13.00 |
| Alpha-ionone | 2.00 |
| Anethole | 10.00 |
| Eugenol | 10.00 |
| 2-Methylundecanal | 4.00 |
| 2-Methyl-3-(4-tert.butylphenyl)propanal | 5.00 |
| Tricyclo[5.2.1.0$^{2.6}$]dec-3-en-9-yl acetate | 10.00 |
| Total | 150.00 |

EXAMPLES

The test applied to a range of common perfumery materials. The results are shown in Table 2.

TABLE 2

Stability data for emulsion systems containing perfumery materials

| Perfumery materials | Test emulsions | | | | | Sum score |
| | 1 | 2 | 3 | 4 | 5 | |
|---|---|---|---|---|---|---|
| 2-Phenylethanol | + | − | − | − | ++ | 3 |
| HCA | + | − | − | + | ++ | 4 |
| Diethyl phthalate | ++ | − | − | − | − | 2 |
| Linalol | − | + | − | − | ++ | 3 |
| Benzyl Salicylate | ++ | − | − | + | + | 4 |
| Tonalid | ++ | + | − | ++ | − | 5 |
| Menthol (laevo) | − | − | − | − | ++ | 2 |
| Carvone (laevo) | ++ | − | − | + | ++ | 5 |
| Galaxolide | − | + | − | + | + | 3 |
| Linalyl acetate | − | − | − | ++ | − | 2 |
| Octan-2-one | − | − | − | + | + | 2 |
| Musk MC4 | ++ | − | − | + | − | 3 |
| Ethylene Brass. | − | − | − | + | + | 2 |
| Celestolide | − | − | − | ++ | + | 3 |
| Hercolyn D | − | ++ | − | ++ | + | 5 |
| Traseolide | − | ++ | − | ++ | − | 4 |
| Cedrol | − | + | − | + | ++ | 4 |
| Vanillin | ++ | − | − | − | − | 2 |
| Sclareol | − | − | − | − | + | 1 |
| Cyclopentadec | ++ | ++ | + | ++ | − | 7 |
| Cinnamic alcohol | − | + | − | − | ++ | 3 |
| Aldehyde C10 | − | + | + | + | + | 4 |

KEY to Table 2
+ = As stable as samples containing cholesterol
++ = More stable than samples containing cholesterol
HCA = Alpha-hexylcinnamic aldehyde
Tonalid = 1,1,2,4,4,7-Hexamethyl-6-acetyltetralin (trademark of PFW Inc.)
Galaxolide = 1,3,4,6,7,8-Hexahydro-4,6,6,7,8,8-hexamethylcyclopenta[g]-2-benzopyran (trademark of IFF Inc.)
Musk MC4 = Ethylene 1,12-dodecanedicate
Ethylene brass = Ethylene brassylate
Celestolid = 4-Acetyl-6-tert.-butyl-1,1-dimethyl-indane (trademark of IFF Inc.)
Hercolyn D = Mixture of methyl tetrahydro- anddihydro-abietate (trademark of Hercules Powder Co.)
Traseolide = 5-Acetyl-3-isopropyl-1,1,2,6-tetramethylindane (trademark of Quest International)
Cyclopentadec. = Cyclopentadecanolide

We claim:
1. An opaque emulsion containing niosomal systems having liquid crystal-like structures comprising a non-aqueous phase, which comprises the following components:
   (a) an emulsifier system, consisting of one or more non-ionic emulsifiers;
   (b) a liquid hydrophobic system, consisting of one or more hydrophobic materials;
   (c) one or more stabilizing perfumery materials;
   (d) one or more optional surfactants, other than non-ionics;
and an aqueous phase which optionally also comprises hydrophilic materials; wherein the emulsifier system is present at 1-30% of the total weight, the aqueous phase is present at 30-98% of the total weight, the liquid hydrophobic system is present at 0.01-50% of the total weight, the stabilizing perfumery material is present at 0.5-25% by weight relative to the emulsifier system, and optional surfactants are present at 0-50% by weight relative to the emulsifier system.

2. An emulsion according to claim 1, wherein the emulsifier system consists of one or more non-ionic emulsifiers is selected from the group consisting of polyethoxylated alcohols, fatty acid esters of polyethylene glycol, glycerol mono-fatty acid esters, sorbitan fatty acid esters and polyethoxylated sorbitan fatty acid esters.

3. An emulsion according to claim 2 wherein the non-ionic emulsifiers is selected from the group consisting of
   i.a. (Polyethoxylated) alcohols of the formula:

$$CH_3-(CH_2)_x-(CH=CH)_y-(CH_2)_z-(O-CH_2-CH_2)_w-OH$$

wherein: w ranges from 0-20, y is 0 or 1; x+z+2y=11-23;
   i.b. Branched (polyethoxylated) fatty alcohols of the formula:

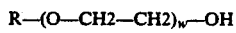
$$R-(O-CH_2-CH_2)_w-OH$$

wherein: R is a branched alkyl group of 12-18 carbon atoms and w is as specified above;
   ii. Glycerol mono-stearate, oleate, palmitate or laurate;
   iii. Fatty acid esters of polyethylene glycol of the formula:

R1—(O—CH2—CH2)w—OH or

R1—(O—CH2—CH2)w—O—R1 wherein R1 is a stearoyl, lauroyl, oleoyl or palmitoyl residue; w ranges from 2-20;

iv. Sorbitan fatty acid mono- and tri-esters of the formula:

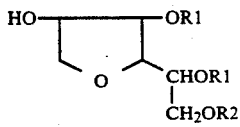

wherein R1 is H or

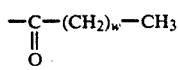

and R2 is

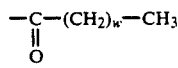

and w ranges from 10-16;

v. Polyethoxylated sorbitan fatty acid esters, of the formula:

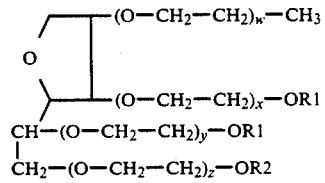

wherein: R1 is H or

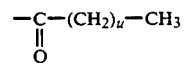

and R2 is

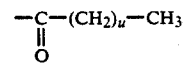

u ranges from 10-16 and (w+x+y+z) is 2-20.

4. An emulsion according to claim 3, wherein the non-ionic emulsifier is a (polyethoxylated) alcohol of the formula:

CH3—(CH2)x—(CH=CH)y—(CH2)z—(O—CH2—CH2)w—OH wherein: w ranges from 0-20, y is 0 or 1; x+z+2y=11-23.

5. An emulsion according to claim 3, wherein the non-ionic emulsifier is glycerol monostearate, glycerol monooleate, glycerol monopalmitate or glycerol monolaurate.

6. An emulsion according to claim 3, wherein the non-ionic emulsifier is a fatty acid esters of polyethylene glycol of the formula:

R1—(O—CH2—CH2)w—OH or

R1—(O—CH2—CH2)w—O—R1 wherein R1 is a stearoyl, lauroyl, oleoyl or palmitoyl residue; w ranges from 2-20.

7. An emulsion according to claim 1, wherein the emulsifier system is present at 1-30% of the total weight; the aqueous phase is present at 40-95% of the total weight; the hydrophobic system is present at 10-50% of the total weight; the stabilizig perfumery materials are present at 5-15% by weight of the emulsifier system and the optional surfactants other than non-ionics are present at 0-20% of the weight of the emulsifier system.

8. An emulsion according to claim 1, wherein the stabilizing perfumery materials selected from the group consisting of 1,1,2,4,4,7-hexamethyl-6-acetyltetralin, carvone, cyclopentadecanolide, and methyl tetrahydro- and dihydro-abietate.

9. A process for preparing stabilized emulsions containing niosomal systems having liquid crystal-like structures comprising an aqueous phase and a non-aqueous phase wherein:
I. the non-aqueous phase is formed by mixing:
(a) An emulsifier system A, present at 1-30% of the total weight with an aqueous phase present at 30-98% of the total weight, consisting of one or more non-ionic emulsifiers;
(b) A liquid hydrophobic system B, present at 0.01-50% of the total weight, consisting of one or more hydrophobic materials;
(c) One or more stabilizing perfumery materials C, present at 0.5-25% by weight relative to the emulsifier system;
(d) one or more optional surfactants D, present at 0-50% by weight relative to the emulsifier system, other than non-ionics;
whilst maintaining the temperature sufficiently high to obtain a homogeneous liquid,
II. the non-aqueous phase is mixed with the aqueous phase which optionally also comprises hydrophilic materials and is maintained at substantially the same temperature as the non-aqueous phase, under shear conditions and for a sufficient time to obtain a stable emulsion, whereafter the emulsion is brought to ambient temperature if necessary.

10. The process according to claim 9, wherein the emulsifier system consists of one or more non-ionic emulsifiers selected from the group consisting of polyethoxylated alcohols, fatty acid esters of polyethylene glycol, glycerol mono-fatty acid esters, sorbitan fatty acid esters and polyethoxylated sorbitan fatty acid esters.

11. The process according to claim 10 wherein the non-ionic emulsifiers is selected from the group consisting of:

i) a) (polyethoxylated) alcohols of the formula:

CH3—(CH2)x—(CH=CH)y—(CH2)z—(O—CH2—CH2)w—OH wherein: w ranges from 0-20, y is 0 or 1; x+z+2y=11-23;

i) b) branched (polyethoxylated) fatty alcohols of the formula:

R—(O—CH2—CH2)w—OH wherein: R is a branched alkyl group of 12-18 carbon atoms and w is as specified above;

ii) glycerol mono-stearate, oleate, palmitate or laurate;

iii) fatty acid esters of polyethylene glycol of the formula:

R1—(O—CH$_2$—CH$_2$)$_w$—OH or

R1—(O—CH$_2$—CH$_2$)$_w$—O—R1 wherein: R1 is a stearoyl, lauroyl, oleoyl or palmitoyl residue; w ranges from 2-20, iv) sorbitan fatty acid mono- and tri-esters of the formula:

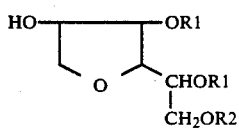

wherein: R1 is H or

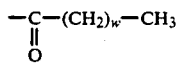

and R2 is

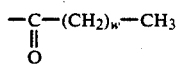

and w ranges from 10-16; and v. Polyethoxylated sorbitan fatty acid esters, of the formula:

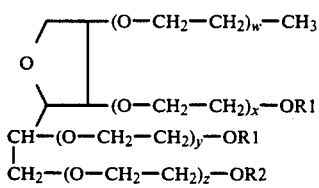

wherein: R1 is H or

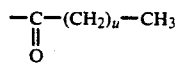

and R2 is

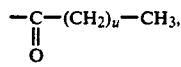

u ranges from 10-16 and (w+x+y+z) is 2-20.

12. The emulsion according to claim 11, wherein the non-ionic emulsifier is a (polyethoxylated) alcohol of the formula:

CH$_3$—(CH$_2$)$_x$—(CH═CH)$_y$—(CH$_2$)$_z$—(O—CH$_2$—CH$_2$)$_w$—OH wherein: w ranges from 0-20, y is 0 or 1; x+z+2y=1-1-23.

13. The process according to claim 11, wherein the non-ionic emulsifier is glycerol monostearate, glycerol monooleate, glyerol monopalmitate or glycerol monolaurate.

14. The process according to claim 11, wherein the non-ionic emulsifier is a fatty acid esters of polyethylene glycol of the formula:

R1—(O—CH$_2$—CH$_2$)$_w$—OH or

R1—(O—CH$_2$—CH$_2$)$_w$—O—R1 wherein: R1 is a stearoyl, lauroyl, oleoyl or palmitoyl residue; w ranges from 2-20.

15. The process according to claim 9, wherein the emulsifier system is present at 1-30% of the total weight; the aqueous phase is present at 40-95% of the total weight; the hydorphobic system is present at 10-50% of the total weight; the stabilizing perfumery materials are present at 5-15% by weight of the emulsifier system and the optional surfactants other than non-ionics are present at 0-20% of the weight of the emulsifier system.

16. The process according to claim 9, wherein the stabilizing perfumery materials is selected from the group consisting of 1,1,2,4,4,7-hexamethyl-6-acetyltetralin, carbone, cyclopentadecanolide, and methyl tetrahydro- and dihydro-abietate.

* * * * *